United States Patent [19]

Bussler

[11] Patent Number: 5,256,630
[45] Date of Patent: * Oct. 26, 1993

[54] SAFENING MIXTURES OF SULFONYLUREA AND ACETANILIDE HERBICIDES

[75] Inventor: Brett H. Bussler, St. Louis Park, Minn.

[73] Assignee: Monsanto Company, St. Louis, Mo.

[*] Notice: The portion of the term of this patent subsequent to Jul. 6, 2010 has been disclaimed.

[21] Appl. No.: 459,228

[22] Filed: Dec. 29, 1989

Related U.S. Application Data

[63] Continuation-in-part of Ser. No. 212,621, Jul. 1, 1988, which is a continuation-in-part of Ser. No. 84,786, Aug. 13, 1987, abandoned.

[51] Int. Cl.$^5$ .............................................. A01N 43/48
[52] U.S. Cl. .................................... 504/134; 504/130; 504/131; 504/132; 504/133; 504/136; 504/137; 504/138; 504/139; 504/140; 504/141; 504/148; 504/149
[58] Field of Search ................. 71/DIG. 1, 118, 92, 71/88; 504/130, 134, 139, 149, 131, 132, 133, 136, 137, 138, 148, 141, 140

[56] References Cited

U.S. PATENT DOCUMENTS

| 3,547,620 | 12/1970 | Olin | 71/118 |
| 3,989,503 | 11/1976 | Pallos et al. | 71/88 |
| 4,840,663 | 6/1989 | Quadranti et al. | 71/93 |
| 4,877,442 | 11/1989 | Hillemann | 71/92 |

FOREIGN PATENT DOCUMENTS

| 6700286 | 7/1987 | Australia | 71/65 |
| 0304409 | 2/1989 | European Pat. Off. | |

OTHER PUBLICATIONS

CA 89:24451m (1978) Maksudov et al.
"Sofite ® Super: Broad Spectrum Weed Management for Wet Sown Rice in S.E. Asia, Twelfth Conference; (1989) Asia-Pacific Weed Science Society", pp. 165-170.

Primary Examiner—Richard L. Raymond
Assistant Examiner—Brian M. Burn
Attorney, Agent, or Firm—William I. Andress

[57] ABSTRACT

The disclosure herein relates to safening crops from injury by herbicidal mixtures of sulfonylurea and acetanilide herbicides by means of 5-heterocyclyl-substituted dichloroacetamide antidotes.

19 Claims, No Drawings

SAFENING MIXTURES OF SULFONYLUREA AND ACETANILIDE HERBICIDES

This application is a continuation-in-part of copending U.S. application Ser. No. 07/212,621 filed Jul. 1, 1988, which is a continuation-in-part of U.S. application Ser. No. 084,786, filed Aug. 13, 1987, now abandoned.

FIELD OF THE INVENTION

The field of the invention contemplated herein pertains to the safening of mixtures of herbicidal compounds with antidotal or safener compounds. Particular herbicides involved are mixtures of sulfonylurea and acetanilide compounds.

BACKGROUND OF THE INVENTION

Many herbicides injure crop plants at herbicide application rates necessary to control weed growth. Accordingly, many herbicides cannot be used for controlling weeds in the presence of certain crops. Uncontrolled weed growth, however, results in lower crop yield and reduced crop quality inasmuch as weeds compete with crops for light, water and soil nutrients. Reduction of herbicidal injury to crops without an unacceptable corresponding reduction of herbicidal action on the weeds can be accomplished by use of crop protectants known as herbicide "antagonists", "antidotes" or "safeners".

Weed control for crops, especially corn crops, is one of the oldest and most highly developed areas in weed science. For a herbicide product to be accepted commercially for corn crops, such herbicide product must provide a relatively high level of control of both grassy and broadleaf weeds in corn, in addition to meeting several other criteria. For example, the herbicide should possess relatively high unit activity so that lower rates of herbicide application are feasible. Lower application rates are desirable in order to minimize exposure of the environment to the herbicide. At the same time, such herbicide must be selective in herbicidal effect so as not to injure the crops. Herbicidal selectivity can be enhanced by use of an appropriate antidote in combination with the herbicide. But identification of an antidote which safens a herbicide or mixture of herbicides in crops is a highly complicated task. Whether a compound or class of compounds provides efficacious antidote or safening activity is not a theoretical determination but must be done empirically. Safening activity is determined empirically by observing the complex interaction of several biological and chemical factors, namely: the type of herbicide compound; the type of weed to be controlled; the type of crop to be protected from weed competition and herbicidal injury; and the antidote compound itself. Moreover, the herbicide and antidote must each possess chemical and physical properties enabling preparation of a stable formulation which is environmentally safe and easy to apply to the field.

Among the various classes of compounds found to be suitable for various herbicidal purposes are the α-haloacetanilides and sulfonylureas. The former herbicides, e.g., alachlor, acetochlor, metolachlor, etc., are excellent preemergence or early post emergence herbicides for controlling annual grasses and many broadleaved weeds in corn, peanuts, soybeans and other crops, while some of the latter herbicides, exemplified by chlorsulfuron ethyl, DPX-M6316, chlorimuron, triasulfuron, metsulfuron methyl, bensulfuron methyl and the like, may be used as a foliar—or soil-applied herbicide suitable for the control of many annual and perennial broadleaved species in asparagus, cereals, grain, corn, sorghum, sugarcane and other crops and woody brush and vine control in pasture, rangeland and cropland. Other sulfonylureas can be used in preplant or preemergence applications.

It is a common agronomic practice to use various antidotal compounds to reduce the phytotoxicity of some herbicides to various crops. For example, fluorazole (active ingredient in SCREEN ® safener) is used as a seed dressing to protect sorghum seed from alachlor (active ingredient in LASSO ® herbicide). Similarly, cyometrinil (active ingredient in CONCEP ® safener) is a corn seed safener for use with metolachlor and oxabetrinil (active ingredient in CONCEP II safener) is used to safen sorghum seed from injury by metolachlor. The compound N,N-diallyl dichloroacetamide (common name R-25788) is used to safen corn from injury by the thiocarbamate 5-ethyl-N,N-dipropylthiocarbamate (active ingredient in ERADICANE ® herbicide) and acetochlor (active ingredient in HARNESS ® herbicide).

It is not known to our knowledge to safen mixtures of sulfonylureas and acetanilides as co-herbicides. Accordingly, it is an object of this invention to provide compositions of those herbicides in combination with antidotes therefor, which compositions are useful to reduce injury to crops, especially corn, due to phytotoxicity of said herbicides.

SUMMARY OF THE INVENTION

The present invention relates to herbicidal compositions comprising mixtures of sulfonylurea and acetanilide herbicides and antidotal compounds therefor to reduce injury to various crops, particularly corn, from the phytotoxic effects of said mixtures when used as such or in combination with other compounds as co-herbicides.

In more particular, in a major aspect, this invention relates to a composition comprising:

(a) a herbicidally-effective amount of a sulfonylurea of the formula

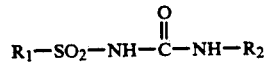

$$R_1-SO_2-NH-\overset{O}{\underset{\|}{C}}-NH-R_2 \qquad I$$

wherein $R_1$ and $R_2$ are independently phenyl, a heterocyclic radical containing up to 10 ring members of which 4 may be O, S or N atoms or said phenyl and heterocyclic radical optionally substituted with halogen, $C_{1-4}$ alkyl, haloalkyl, alkoxy, haloalkoxy, carboxyl or carboalkoxy radicals;

(b) a herbicidally-effective amount of an acetanilide of the formula

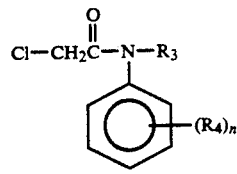

$$Cl-CH_2\overset{O}{\underset{\|}{C}}-N-R_3 \qquad II$$
$$\text{(R}_4\text{)}_n$$

$R_3$ is hydrogen, $C_{1-8}$ alkyl, haloalkyl, alkoxy or alkoxyalkyl, alkenyl, haloalkenyl, alkynyl or haloalkynyl or acylamidoalkyl, having up to 6 carbon atoms, $C_{5-10}$ heterocyclyl or heterocyclylmethyl having O, S, and/or N atoms and which may be substituted with halogen, $C_{1-4}$ alkyl, carbonylalkyl or carbonylalkoxyalkyl, nitro, amino or cyano groups;

$R_4$ is hydrogen, halogen, nitro, amino, $C_{1-6}$ alkyl, haloalkyl, alkoxy or alkoxyalkyl; and n is 0-5 and (c) an antidotally-effective amount of a compound of the formula

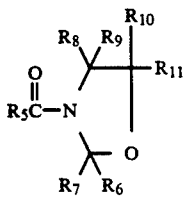

III and agriculturally-acceptable salts thereof wherein $R_5$ is halomethyl;

$R_6$ and $R_7$ are H, $C_{1-4}$ alkyl, haloalkyl, alkoxy or phenyl:

$R_{8-10}$ are H or $C_{1-4}$ alkyl;

$R_{11}$ is a saturated or unsaturated heterocyclic radical containing up to 10 ring atoms of which 3 may be O, S or N atoms, optionally substituted with halogen, $C_{1-4}$ alkyl, haloalkyl, alkoxy or alkoxyalkyl or with oxygen on a ring N atom or $R_{11}$ may be a bicyclic hydrocarbon radical containing up to 10 carbon atoms; and $R_{10}$ and $R_{11}$ may be combined to form a spiroheterocyclic ring as defined for $R_{11}$.

Preferred herbicidal sulfonylureas according to Formula I include:

Benzenesulfonamide, 2-chloro-N-[[(4-methoxy-6-methyl-1,3,5-triazin-2-yl)amino]carbonyl], (common name "chlorsulfuron");

Benzoic acid, 2-[[[[(4-chloro-6-methoxy-2-pyrimidinyl)amino]carbonyl]amino]sulfonyl]ethyl ester, (common name "chlorimuron ethyl");

2-Thiophenecarboxylic acid, 3-[[[[(4,6-dimethoxy-1,3,5-triazin-2-yl)amino]carbonyl]amino]sulfonyl]-, methyl ester, (code number DPX-M6316):

Benzoic acid, 2-[[[[(4,6-dimethyl-2-pyrimidinyl) amino]carbonyl]amino]sulfonyl]methyl ester, (common name "sulfometuron methyl");

Benzenesulfonamide, 2-(2-chloroethoxy)-N-[[(4-methoxy-6-methyl-1,3,5-triazin-2-yl) amino]carbonyl], (common name "triasulfuron"); and Benzoic acid, 2-[[[[(4-methoxy-6-methyl-1,3,5-triazin-2-yl)amino]carbonyl]amino]sulfonyl]methyl ester, (common name "metsulfuron").

Preferred herbicidal acetanilide compounds according to Formula II are those wherein the $R_3$ member is an alkoxyalkyl group having up to 6 carbon atoms and $R_4$ is a $C_{1-6}$ alkyl, alkoxy or alkoxyalkyl radical. The most preferred species are 2-chloro-2'-ethyl-6'-methyl-N-(ethoxymethyl) acetanilide (common name "acetochlor"), 2-chloro-2',6'-diethyl-N-(methoxymethyl)acetanilide (common name "alachlor"), 2-chloro-2',6'-diethyl-N-(butoxymethyl)acetanilide (common name "butachlor"), 2-chloro-2'-ethyl-6'-methyl-N-(1-methyl-2-methoxyethyl) acetanilide (common name "metolachlor"), 2-chloro-2',6'-diethyl-N-(n-propoxyethyl)acetanilide (common name "pretilachlor"), and 2-chloro-2',6'-dimethyl-N-(pyrazolylmethyl)acetanilide (common name "metazachlor").

Other important acetanilide herbicides are the following:

2-chloro-N-isopropylacetanilide (common name "propachlor");

2-chloro-N-(ethoxymethyl)-6'-ethyl-o-acetotoluidide (common name "acetochlor"); ethyl ester of N-chloroacetyl-N-(2,6-di-ethylphenyl)glycine (common name "diethatyl ethyl");

2-chloro-N-(2,6-dimethylphenyl)-N-(2-methoxyethyl)acetamide (common name "dimethachlor");

2-chloro-2'-methyl-6'-methoxy-N-(isopropoxymethyl)acetanilide;

2-chloro-N(2,6-dimethyl-1-cyclohexen-1-yl)-N-(1H-pyrazol-1-ylmethyl)acetamide;

2-chloro-6'-trifluoromethyl-N-(isopropoxymethyl) acetanilide;

2-chloro-2'-methyl-6'-trifluoromethyl-N-(ethoxymethyl)acetanilide;

2-chloro-2'-ethyl-6'-trifluoromethyl-N-(1-pyrazolyl-1-ylmethyl)acetanilide;

2-chloro-N-isopropyl-1-(3,5,5-trimethylcyclohexen-1-yl)acetamide (common name "trimexachlor").

Preferred antidotal members according to Formula III are those wherein $R_{11}$ is one of said heterocyclic members and $R_6$ and $R_7$ are independently methyl or trifluoromethyl.

Preferred antidotal compounds according to Formula III are the following compounds:

Oxazolidine, 3-(dichloroacetyl)-2,2-dimethyl-5-(2-furanyl)-,

Oxazolidine, 3-(dichloroacetyl)-2,2-dimethyl-5-(2-thienyl)-,

Pyridine, 3-[3-(dichloroacetyl)-2,2-dimethyl-5-oxazolidinyl]-.

The herbicidal and antidotal compounds of Formulae I-III are known in the art. The sub-group of 1,3-oxazolidine dichloroacetamides of Formula III are the subject of copending application Ser. No. 07/212,621, of common assignment herewith, priority application for EP 304409 published Feb. 22, 1989 and South African Patent No. 5997 dated Jun. 28, 1989.

The term "haloalkyl" embraces radicals wherein any one or more of the carbon atoms, preferably from 1 to 4 in number, is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are perhaloalkyl groups such as trifluoromethyl and perfluoroethyl groups.

Preferred haloalkyl R members are dihalomethyl, particularly dichloromethyl, while the preferred haloalkyl $R_1$ member is a tri-halogenated methyl radical, preferably trifluoromethyl.

Where the term "alkyl" is used either alone or in compound form (as in "haloalkyl"), it is intended to embrace linear or branched radicals having up to four carbon atoms, the preferred members being methyl and ethyl.

By "agriculturally-acceptable salts" of the compounds defined by the above formula is meant a salt or salts which readily ionize in aqueous media to form a cation of said compounds and a salt anion, which salts have no deleterious effect on the antidotal properties of said compounds or of the herbicidal properties of a given herbicide and which permit formulation of the herbicide-antidote composition without undue problems of mixing, suspension, stability, applicator equipment use, packaging, etc.

By "antidotally-effective" is meant the amount of antidote required to reduce the phytotoxicity level or effect of a herbicide, preferably by at least 10% or 15%, but naturally the greater the reduction in herbicidal injury the better.

By "herbicidally-effective" is meant the amount of herbicide required to effect a meaningful injury or destruction to a significant portion of affected undesirable plants or weeds. Although of no hard and fast rule, it is desirable from a commercial viewpoint that 80–85% or more of the weeds be destroyed, although commercially significant suppression of weed growth can occur at much lower levels, particularly with some very noxious, herbicide-resistant plants.

The terms "antidote", "safening agent", "safener", "antagonistic agent", "interferant", "counter-agent", "crop protectant" and "crop protective", are often-used terms denoting a compound capable of reducing the phytotoxicity of a herbicide to a crop plant or crop seed. The terms "crop protectant" and "crop protective" are sometimes used to denote a composition containing as the active ingredients, a herbicide-antidote combination which provides protection from competitive weed growth by reducing herbicidal injury to a valuable crop plant while at the same time controlling or suppressing weed growth occurring in the presence of the crop plant. Antidotes protect crop plants by interfering with the herbicidal action of a herbicide on the crop plants so as to render the herbicide selective to weed plants emerging or growing in the presence of crop plants.

As used herein, the singular "herbicide" where appropriate denotes mixtures or combinations of sulfonylurea and α-haloacetanilide herbicides.

As further detailed infra, while not necessary, the composition containing the herbicide-antidote combination may also contain other additaments, e.g., biocides such as insecticides, fungicides, nematocides, miticides, etc., fertilizers, inert formulation aids, e.g., surfactants, emulsifiers, defoamers, dyes, etc.

Combinations may be made of any one or more of the described antidote compounds with any one or more of the mixtures of herbicide compounds of Formulae I and II.

It will be recognized by those skilled in the art that all herbicides have varying degrees of phytotoxicity to various plants because of the sensitivity of the plant to the herbicide. Thus, e.g., although certain crops such as corn and soybeans have a high level of tolerance (i.e., low sensitivity) to the phytotoxic effect of alachlor, other crops, e.g., milo (grain sorghum), rice and wheat, have a low level of tolerance (i.e., high sensitivity) to the phytotoxic effects of alachlor. The same type of sensitivity to herbicides as shown by crop plants is also exhibited by weeds, some of which are very sensitive, others very resistant to the phytotoxic effects of the herbicide.

When the sensitivity of a crop plant to a herbicide is low, whereas the sensitivity of a weed to that herbicide is high, the "selectivity factor" of the herbicide for preferentially injuring the weed while not injuring the crop is high.

In an analogous manner, but more complex, an antidotal compound may, and commonly does, have varying degrees of crop protective effect against different herbicides in different crops. Accordingly, as will be appreciated by those skilled in the art, the various antidotes of this invention, as with all classes of antidotal compounds, will have greater or lesser crop safening effects against various herbicides in various crops than in others. Thus, while a given antidotal compound may have no crop protective ability against a given herbicide in a given crop, that same antidotal compound may have a very high crop protective ability against the same given herbicide in a different crop or against a different herbicide in the same crop. This is an expected phenomenon.

DETAILED DESCRIPTION OF THE INVENTION

Biological Evaluation

Effective weed control coupled with low crop injury is a result of treatment of a plant locus with a combination of herbicide compound and antidote compound. By application to the "plant locus" is meant application to the plant growing medium, such as soil, as well as to the seeds, emerging seedlings, roots, stems, leaves, or other plant parts.

The phrase "combination of herbicide compound and antidote compound" embraces mixtures of sulfonylurea and acetanilide herbicides, together with the antidote and various methods of treatment. For example, the soil of a plant locus may be treated with a "tank-mix" composition containing a mixture of the herbicide and the antidote which is "in combination". Or, the soil may be treated with the herbicide and antidote compounds separately so that the "combination" is made on, or in, the soil. After such treatments of the soil with a mixture of herbicide and antidote or by separate or sequential application of the herbicide and antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and antidote-coated seed are in the soil. Also contemplated as a "combination" is a commercially-convenient association or presentation of herbicide and antidote. For example, the herbicide and antidote components in concentrated form may be contained in separate containers, but such containers may be presented for sale or sold together as a "combination". Or, the herbicide and antidote components in concentrated form may be in a mixture in a single container as a "combination". Either such "combination"

may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

In the foregoing description of various modes of application of the herbicide-antidote combinations, it is inherent that each form of application requires that in some manner, the herbicide and antidote will physically combine to form a "composition" of those agents.

The amount of antidote employed in the methods and compositions of the invention will vary depending upon the particular herbicide with which the antidote is employed, the rate of application of the herbicide, the particular crop to be protected, and the manner of application to the plant locus. In each instance the amount of antidote employed is a safening-effective amount, that is, the amount which reduces, or protects against, crop injury that otherwise would result from the presence of the herbicide. The amount of antidote employed will be less than an amount that will substantially injure the crop plant.

The antidote can be applied to the crop plant locus in a mixture with the selected herbicide. For example, where the crop seed is first planted, a suitable mixture of antidote and herbicide, whether in a homogeneous liquid, emulsion, suspension or solid form, can be applied to the surface of, or incorporated in, the soil in which the seed has been planted. Or, the herbicide-antidote mixture may be applied to the soil, and then the seed thereafter "drilled" into the soil below the soil layer containing the herbicide-antidote mixture. The herbicide will reduce or eliminate the presence of undesirable weed plants. Where the herbicide would by itself injure the crop seedlings, the presence of the antidote will reduce or eliminate the injury to the crop seed caused by the herbicide. It is not essential that the application of herbicide and the antidote to the plant locus be made using the selected herbicide and antidote in the form of a mixture or composition. The herbicide and the antidote may be applied to the plant locus in a sequential manner. For example, the antidote may be first applied to the plant locus and thereafter the herbicide is applied. Or, the herbicide may be first applied to the plant locus and thereafter the antidote is applied.

The ratio of herbicide to antidote may vary depending upon the crop to be protected, weed to be inhibited, herbicide used, etc., but normally a herbicide-to-antidote ratio ranging from 1:25-to-60:1 (preferably 1:5-to-30:1) parts by weight may be employed, although much higher rates of antidote may be used, e.g., 1:100–1:300 parts by weight of herbicide-to-antidote. The ratio of sulfonylurea:acetanilide will vary depending upon the particular crop/weed spectrum to be treated and will be generally within a broad range of from 0.5:1.0 to 1.0:100 parts by weight. As indicated above, the antidote may be applied to the plant locus in a mixture, i.e., a mixture of a herbicidally-effective amount of herbicides and a safening-effective amount of an antidote, or sequentially, i.e., the plant locus may be treated with an effective amount of the herbicide followed by a treatment with the antidote or vice versa. In general, effective herbicidal amounts are in the range of about 0.03 to about 12 kilograms/hectare, but rates as low as 0.004 kg/ha may be used effectively. The preferred range of rate of application is from about 0.1 to about 10 kg/ha. Preferably, antidote application rates range from about 0.5 kg/ha down to about 0.05 kg/ha. It will be appreciated that at times amounts either below or above these herbicide and antidote ranges will be necessary to obtain the best results. The selection of the herbicide to inhibit the emergence and growth of weeds depends upon the species of weeds to be controlled and the crop to be protected.

The application of the antidote can be made directly to the seed before planting. In this practice, a quantity of crop seed is first coated with the antidote. The coated seed is thereafter planted. The herbicide may be applied to the soil before or after the coated seed is planted.

In field applications, the herbicide, antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

Evaluations of safening activity of representative sulfonylurea and acetanilide mixtures and antidote compounds according to this invention were carried out using the specific procedures of Examples 1 and 2 below in greenhouse testing. Measurements of biological response as reported in Tables 1 and 2 were made in the following manner. A visual comparison was made between a crop and weed plant treated with each herbicide alone, with a mixture of the two herbicides, and with the two herbicides containing an antidote. The percent injury or inhibition to growth of the treated plants is noted in the columns under the plants. The degree of reduction of herbicide injury provided by the antidote is indicated by the difference in injury to the plants treated without and with an antidote present.

Listed below are the names of antidotes used to test combinations of selected sulfonylureas and acetochlor as a representative α-haloacetanilide. These antidotes were formulated in a suitable solvent, e.g., acetone, and, similarly as with commercially-available formulations of the sulfonylureas and in-house preparations of acetochlor, formulated to a concentration corresponding to the desired application rate per hectare.

| Antidote No. | Name |
|---|---|
| 1 | Oxazolidine, 3-(dichloroacetyl)-2,2-dimethyl-5-(2-thienyl)-, |
| 2 | Oxazolidine, 3-(dichloroacetyl)-5-(2-furanyl)- |

-continued

| Antidote No. | Name |
|---|---|
| 3 | 2,2-dimethyl-, Pyridine, 3-[3-(dichloroacetyl)-2,2-dimethyl-5-oxoazolidinyl]-. |

EXAMPLE 1

The procedure in this example is designed to test the interaction between herbicide and antidote when both are incorporated in a soil cover layer before emergence of crop and weed species. The sulfonylurea herbicide in this example was DPX-M6316 mixed with acetochlor as a co-herbicide. The numbered antidotes and herbicides are identified above.

Containers were filled and compacted with a fumigated silt loam top soil to a depth of about 1.3 cm from the top of the container. A first container was designated as an untreated control, a second container was designated as a herbicide control, and a third container was designated as a herbicide+antidote test container. Each of the containers was seeded with a crop species. A measured amount of each herbicide dispersed or dissolved in acetone or water was applied to a measured quantity of soil. To this same quantity of soil treated with herbicide, there was added a measured amount of antidote dispersed or dissolved in acetone or water. The quantity of soil treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers. The cover layer of the first container was not treated with herbicide or antidote. The cover layer of the second container had a measured quantity of both herbicides alone incorporated therein. Each container received 0.6 cm overhead irrigation. The containers were then placed on a bench in a greenhouse and sub-irrigated as required for the duration of the test. Plant response was observed about three weeks after initial treatment. Results are reported in Table 1, wherein the weed in the test, barnyardgrass has the symbol ("BYG"). The first eight treatments (without the antidote) are the average of three replications and all others two replications.

TABLE 1

| Acetochlor Rate (Kg/Ha) | DPX-M6316 Rate (Kg/Ha) | Antidote No. | Rate (Kg/Ha) | % Injury Corn | BYG |
|---|---|---|---|---|---|
| 4.48 | — | — | — | 32 | 100 |
| 8.96 | — | — | — | 57 | 100 |
| — | 1.12 | — | — | 83 | 50 |
| — | 0.28 | — | — | 47 | 45 |
| 4.48 | 1.12 | — | — | 92 | 100 |
| 4.48 | 0.28 | — | — | 68 | 100 |
| 8.96 | 1.12 | — | — | 97 | 100 |
| 8.96 | 0.28 | — | — | 80 | 100 |
| — | — | 1 | 8.96 | 0 | 0 |
| 4.48 | — | 1 | 8.96 | 5 | 100 |
| 4.48 | — | 1 | 2.24 | 13 | 100 |
| 4.48 | — | 1 | 0.56 | 5 | 100 |
| 8.96 | — | 1 | 8.96 | 13 | 100 |
| 8.96 | — | 1 | 2.24 | 20 | 100 |
| 8.96 | — | 1 | 0.56 | 40 | 100 |
| — | 1.12 | 1 | 8.96 | 33 | 25 |
| — | 1.12 | 1 | 2.24 | 50 | 53 |

TABLE 1-continued

| Acetochlor Rate (Kg/Ha) | DPX-M6316 Rate (Kg/Ha) | Antidote No. | Rate (Kg/Ha) | % Injury Corn | BYG |
|---|---|---|---|---|---|
| — | 1.12 | 1 | 0.56 | 40 | 55 |
| — | 0.28 | 1 | 8.96 | 3 | 0 |
| — | 0.28 | 1 | 2.24 | 0 | 35 |
| — | 0.28 | 1 | 0.56 | 8 | 65 |
| 4.48 | 1.12 | 1 | 8.96 | 48 | 100 |
| 4.48 | 0.28 | 1 | 8.96 | 20 | 100 |
| 8.96 | 1.12 | 1 | 8.96 | 55 | 100 |
| 8.96 | 0.28 | 1 | 8.96 | 13 | 100 |
| 4.48 | 1.12 | 1 | 2.24 | 50 | 98 |
| 4.48 | 0.28 | 1 | 2.24 | 25 | 100 |
| 8.96 | 1.12 | 1 | 2.24 | 80 | 100 |
| 8.96 | 0.28 | 1 | 2.24 | 10 | 100 |
| 4.48 | 1.12 | 1 | 0.56 | 30 | 98 |
| 4.48 | 0.28 | 1 | 0.56 | 20 | 100 |
| 8.96 | 1.12 | 1 | 0.56 | 73 | 100 |
| 8.96 | 0.28 | 1 | 0.56 | 28 | 100 |
| — | — | 2 | 8.96 | 0 | 0 |
| 4.48 | — | 2 | 8.96 | 0 | 98 |
| 4.48 | — | 2 | 2.24 | 8 | 100 |
| 4.48 | — | 2 | 0.56 | 18 | 100 |
| 8.96 | — | 2 | 8.96 | 15 | 100 |
| 8.96 | — | 2 | 2.24 | 18 | 100 |
| 8.96 | — | 2 | 0.56 | 20 | 100 |
| — | 1.12 | 2 | 8.96 | 23 | 30 |
| — | 1.12 | 2 | 2.24 | 43 | 75 |
| — | 1.12 | 2 | 0.56 | 58 | 85 |
| — | 0.28 | 2 | 8.96 | 10 | 50 |
| — | 0.28 | 2 | 2.24 | 0 | 43 |
| — | 0.28 | 2 | 0.56 | 3 | 48 |
| 4.48 | 1.12 | 2 | 8.96 | 28 | 98 |
| 4.48 | 0.28 | 2 | 8.96 | 13 | 100 |
| 8.96 | 1.12 | 2 | 8.96 | 55 | 100 |
| 8.96 | 0.28 | 2 | 8.96 | 15 | 100 |
| 4.48 | 1.12 | 2 | 2.24 | 63 | 100 |
| 4.48 | 0.28 | 2 | 2.24 | 18 | 98 |
| 8.96 | 1.12 | 2 | 2.24 | 45 | 98 |
| 8.96 | 0.28 | 2 | 2.24 | 35 | 100 |
| 4.48 | 1.12 | 2 | 0.56 | 30 | 100 |
| 4.48 | 0.28 | 2 | 0.56 | 10 | 100 |
| 8.96 | 1.12 | 2 | 0.56 | 60 | 100 |
| 8.96 | 0.28 | 2 | 0.56 | 35 | 100 |
| — | — | 3 | 8.96 | 0 | 0 |
| 4.48 | — | 3 | 8.97 | 3 | 100 |
| 4.48 | — | 3 | 2.24 | 8 | 100 |
| 4.48 | — | 3 | 0.56 | 20 | 100 |
| 8.96 | — | 3 | 8.96 | 13 | 100 |
| 8.96 | — | 3 | 2.24 | 23 | 100 |
| 8.96 | — | 3 | 0.56 | 13 | 100 |
| — | 1.12 | 3 | 8.96 | 8 | 30 |
| — | 1.12 | 3 | 2.24 | 28 | 50 |
| 8.96 | 1.12 | 3 | 0.56 | 28 | 55 |
| 8.96 | 0.28 | 3 | 8.96 | 3 | 68 |
| — | 0.28 | 3 | 2.24 | 3 | 55 |
| — | 0.28 | 3 | 0.56 | 0 | 65 |
| 4.48 | 1.12 | 3 | 8.96 | 80 | 98 |
| 4.48 | 0.28 | 3 | 8.96 | 5 | 100 |
| 8.96 | 1.12 | 3 | 8.96 | 35 | 100 |
| 8.96 | 0.28 | 3 | 8.96 | 33 | 100 |
| 4.48 | 1.12 | 3 | 2.24 | 63 | 98 |
| 4.48 | 0.28 | 3 | 2.24 | 5 | 100 |
| 8.96 | 1.12 | 3 | 2.24 | 55 | 100 |
| 8.96 | 0.28 | 3 | 2.24 | 10 | 100 |
| 4.48 | 1.12 | 3 | 0.56 | 35 | 100 |
| 4.48 | 0.28 | 3 | 0.56 | 20 | 100 |
| 8.96 | 1.12 | 3 | 0.56 | 55 | 100 |
| 8.96 | 0.28 | 3 | 0.56 | 8 | 100 |

Referring to the data in Table 1 it is noted that all three antidotes reduced injury to corn from combinations of acetochlor and DPX-M6316. Antidote No. 2 was most active, reducing injury to corn from 68% to 10% when the antidote was present at 0.56 kg/ha and 4.48 kg/ha of acetochlor and 0.28 kg/ha of DPX-M6316 were present. Weed control was maintained at high levels.

EXAMPLE 2

The procedure in this example followed that in Example 1, except the sulfonylurea herbicide in this test was chlorimuron ethyl. Test data are shown in Table 2.

TABLE 2

| Acetochlor Rate (Kg/Ha) | Chlorimuron ethyl Rate (Kg/Ha) | Antidote No. | Rate (Kg/Ha) | % Injury Corn | % Injury BYG |
|---|---|---|---|---|---|
| 4.48 | — | — | — | 27 | 100 |
| 8.96 | — | — | — | 60 | 100 |
| — | 0.28 | — | — | 95 | 88 |
| — | 0.07 | — | — | 85 | 92 |
| 4.48 | 0.28 | — | — | 97 | 100 |
| 4.48 | 0.07 | — | — | 87 | 100 |
| 8.96 | 0.28 | — | — | 97 | 100 |
| 8.96 | 0.07 | — | — | 77 | 100 |
| — | — | 1 | 8.96 | 0 | 48 |
| 4.48 | — | 1 | 8.96 | 0 | 100 |
| 4.48 | — | 1 | 2.24 | 20 | 100 |
| 4.48 | — | 1 | 0.56 | 8 | 100 |
| 8.96 | — | 1 | 8.96 | 3 | 100 |
| 8.96 | — | 1 | 2.24 | 15 | 100 |
| 8.96 | — | 1 | 0.56 | 25 | 100 |
| 8.96 | 0.28 | 1 | 8.96 | 45 | 63 |
| — | 0.28 | 1 | 2.24 | 70 | 88 |
| — | 0.28 | 1 | 0.56 | 53 | 80 |
| — | 0.07 | 1 | 8.96 | 5 | 0 |
| — | 0.07 | 1 | 2.24 | 5 | 15 |
| — | 0.07 | 1 | 0.56 | 3 | 85 |
| 4.48 | 0.28 | 1 | 8.96 | 45 | 100 |
| 4.48 | 0.07 | 1 | 8.96 | 5 | 98 |
| 8.96 | 0.28 | 1 | 8.96 | 40 | 100 |
| 8.96 | 0.07 | 1 | 8.96 | 10 | 100 |
| 4.48 | 0.28 | 1 | 2.24 | 40 | 95 |
| 4.48 | 0.07 | 1 | 2.24 | 8 | 98 |
| 8.96 | 0.28 | 1 | 2.24 | 63 | 100 |
| 8.96 | 0.07 | 1 | 2.24 | 18 | 100 |
| 4.48 | 0.28 | 1 | 0.56 | 68 | 100 |
| 4.48 | 0.07 | 1 | 0.56 | 18 | 100 |
| 8.96 | 0.28 | 1 | 0.56 | 80 | 100 |
| 8.96 | 0.07 | 1 | 0.56 | 20 | 100 |
| — | — | 2 | 8.96 | 0 | 43 |
| 4.48 | — | 2 | 8.96 | 3 | 100 |
| 4.48 | — | 2 | 2.24 | 3 | 100 |
| 4.48 | — | 2 | 0.56 | 0 | 98 |
| 8.96 | — | 2 | 8.96 | 0 | 100 |
| 8.96 | — | 2 | 2.24 | 0 | 100 |
| 8.96 | — | 2 | 0.56 | 3 | 100 |
| — | 0.28 | 2 | 8.96 | 20 | 58 |
| — | 0.28 | 2 | 2.24 | 25 | 75 |
| — | 0.28 | 2 | 0.56 | 20 | 65 |
| — | 0.07 | 2 | 8.96 | 8 | 25 |
| — | 0.07 | 2 | 2.24 | 8 | 8 |
| — | 0.07 | 2 | 0.56 | 3 | 40 |
| 4.48 | 0.28 | 2 | 8.96 | 45 | 95 |
| 4.48 | 0.07 | 2 | 8.96 | 5 | 100 |
| 8.96 | 0.28 | 2 | 8.96 | 40 | 100 |
| 8.96 | 0.07 | 2 | 8.96 | 15 | 98 |
| 4.48 | 0.28 | 2 | 2.24 | 8 | 100 |
| 4.48 | 0.07 | 2 | 2.24 | 5 | 95 |
| 8.96 | 0.28 | 2 | 2.24 | 35 | 100 |
| 8.96 | 0.07 | 2 | 2.24 | 8 | 100 |
| 4.48 | 0.28 | 2 | 0.56 | 30 | 95 |
| 4.48 | 0.07 | 2 | 0.56 | 30 | 100 |
| 8.96 | 0.28 | 2 | 0.56 | 78 | 100 |
| 8.96 | 0.07 | 2 | 0.56 | 8 | 100 |
| — | — | 3 | 8.96 | 0 | 30 |
| 4.48 | — | 3 | 8.96 | 0 | 100 |
| 4.48 | — | 3 | 2.24 | 23 | 100 |
| 4.48 | — | 3 | 0.56 | 3 | 100 |
| 8.96 | — | 3 | 8.96 | 8 | 100 |
| 8.96 | — | 3 | 2.24 | 20 | 100 |
| 8.96 | — | 3 | 0.56 | 20 | 100 |
| — | 0.28 | 3 | 8.96 | 10 | 90 |
| — | 0.28 | 3 | 2.24 | 28 | 88 |
| — | 0.28 | 3 | 0.56 | 30 | 90 |
| — | 0.07 | 3 | 8.96 | 8 | 10 |
| — | 0.07 | 3 | 2.24 | 10 | 25 |
| — | 0.07 | 3 | 0.56 | 18 | 75 |
| 4.48 | 0.28 | 3 | 8.96 | 40 | 100 |
| 4.48 | 0.07 | 3 | 8.96 | 18 | 98 |
| 8.96 | 0.28 | 3 | 8.96 | 15 | 83 |
| 8.96 | 0.07 | 3 | 8.96 | 15 | 100 |
| 4.48 | 0.28 | 3 | 2.24 | 65 | 100 |
| 4.48 | 0.07 | 3 | 2.24 | 10 | 98 |
| 8.96 | 0.28 | 3 | 2.24 | 55 | 100 |
| 8.96 | 0.07 | 3 | 2.24 | 23 | 98 |
| 4.48 | 0.28 | 3 | 0.56 | 53 | 100 |
| 4.48 | 0.07 | 3 | 0.56 | 28 | 100 |
| 8.96 | 0.28 | 3 | 0.56 | 50 | 100 |
| 8.96 | 0.07 | 3 | 0.56 | 13 | 100 |

The data in Table 2 show that all three antidotes in the test exhibited safening of mixtures of acetochlor and chlorimuron ethyl, as well as for each herbicide alone. Overall, Antidote No. 2 was most active, reducing injury to corn from 4.48 kg/ha of acetochlor plus 0.28 kg/ha chlorimuron ethyl from 95% to 30% with 0.56 kg/ha of the antidote. Again, weed injury was maintained at a high level.

Herbicidal formulations of the types described above may be exemplified in several illustrative embodiments below.

| | | Weight Percent |
|---|---|---|
| I. Suspoemulsion Concentrates | | |
| A. | DPX-M6316 | 10.0 |
| | Antidote No. 1 | 15.0 |
| | Acetochlor | 20.0 |
| | Nonylphenol ethoxylate (9.5 mole) (Sterox NJ) | 5.0 |
| | Sodium lignosulfonate (Reax 88B) | 2.0 |
| | Water | 48.0 |
| | | 100.0 |
| B. | Chlorimuron ethyl | 20.0 |
| | Antidote No. 1 | 25.0 |
| | Metolachlor | 15.0 |
| | Sodium dioctylsulfosuccinate Aerosol OT | 4.0 |
| | Water | 36.0 |
| | | 100.0 |
| C. | Chlorsulfuron | 20.0 |
| | Antidote No. 2 | 15.0 |
| | Metolachlor | 40.0 |
| | Sodium n-methyl n-oleyl taurate (Igepon T-77) | 3.0 |
| | Water | 22.0 |
| | | 100.0 |
| D. | Metsulfuron | 10.0 |
| | Antidote No. 3 | 10.0 |
| | Acetochlor | 25.0 |
| | Atlox 3437F | 4.0 |
| | Water | 51.0 |
| | | 100.0 |
| E. | Sulfometuron | 2.5 |
| | Antidote No. 2 | 15.0 |
| | Alachlor | 10.0 |
| | Atlox 3437F | 2.0 |
| | Monochlorobenzene | 7.0 |
| | Water | 53.5 |
| | | 100.0 |
| F. | Triasulfuron | 5.0 |
| | Acetochlor | 15.0 |
| | Antidote No. 1 | 10.0 |
| | Atlox 3437 | 1.0 |
| | Water | 69.0 |
| | | 100.0 |
| G. | Chlorimuron ethyl | 10.0 |
| | Antidote No. 2 | 20.0 |

-continued

| | | Weight Percent |
|---|---|---|
| | Metolachlor | 15.0 |
| | Calcium dodecylsufonate polyether alcohol blend | 4.0 |
| | Water | 51.0 |
| | | 100.0 |
| H. | DPX-M3616 | 10.0 |
| | Alachlor | 15.0 |
| | Monochlorobenzene | 7.0 |
| | Antidote No. 2 | 25.0 |
| | Polyoxyethylene/polyoxypropylene block with butanol (e.g., Tergitol ® XH) | 5.0 |
| | Water | 38.0 |
| | | 100.0 |
| I. | Sulfometuron | 10.0 |
| | Acetochlor | 10.0 |
| | Antidote No. 3 | 15.0 |
| | Polyoxyethylene/polyoxypropylene block copolymer with butanol | 4.0 |
| | Water | 61.0 |
| | | 100.0 |
| J. | Chlorimuron | 5.0 |
| | Alachlor | 15.0 |
| | Monochlorobenzene | 7.0 |
| | Antidote No. 3 | 15.0 |
| | Atlox 3437F | 4.0 |
| | Water | 54.0 |
| | | 100.0 |
| K. | Chlorsulfuron | 10.0 |
| | Acetochlor | 10.0 |
| | Antidote No. 1 | 15.0 |
| | FloMo 60H | 3.0 |
| | Water | 62.0 |
| | | 100.0 |

II. Wettable Powders

| A. | Chlorimuron | 15.0 |
|---|---|---|
| | Acetochlor | 15.0 |
| | Antidote No. 2 | 20.0 |
| | Sodium dioctylsulfosuccinate | 2.75 |
| | Calcium lignosulfonate | 1.25 |
| | Amorphous silica synthetic | 51.00 |
| | | 100.0 |
| B. | Triasulfuron | 10.0 |
| | Metolachlor | 10.0 |
| | Antidote No. 3 | 15.0 |
| | Sodium lignosulfonate | 2.0 |
| | Sodium N-methyl-N-oleyl-taurate | 1.0 |
| | Kaolinite clay | 62.0 |
| | | 100.0 |

III. Dusts

| A. | Metsulfuron | 2.0 |
|---|---|---|
| | Metolachlor | 4.0 |
| | Antidote No. 1 | 5.0 |
| | Attapulgite | 89.0 |
| | | 100.0 |
| B. | Sulfometuron | 10.0 |
| | Acetochlor | 10.0 |
| | Antidote No. 2 | 30.0 |
| | Montmorillonite | 50.0 |
| | | 100.0 |
| C. | DPX-M6316 | 10.0 |
| | Metolachlor | 10.0 |
| | Antidote No. 2 | 15.0 |
| | Bentonite | 65.0 |
| | | 100.0 |
| D. | Chlorimuron ethyl | 2.0 |
| | Pretilachlor | 10.0 |
| | Antidote No. 1 | 10.0 |
| | Diatomaceous earth | 68.0 |
| | | 100.0 |

IV. Granules

| A. | DPX-M6316 | 4.0 |
|---|---|---|
| | Alachlor | 8.0 |
| | Antidote No. 2 | 16.0 |
| | Granular attapulgite (20/40 mesh) | 72.0 |

-continued

| | | Weight Percent |
|---|---|---|
| | | 100.0 |
| B. | Sulfometuron | 8.0 |
| | Alachlor | 10.0 |
| | Antidote No. 1 | 15.0 |
| | Diatomaceous earth 20/40 | 67.0 |
| | | 100.0 |
| C. | Triasulfuron | 5.0 |
| | Acetochlor | 15.0 |
| | Antidote No. 2 | 10.0 |
| | Bentonite (20/40) | 70.0 |
| | | 100.0 |
| D. | Metsulfuron | 10.0 |
| | Metolachlor | 15.0 |
| | Antidote No. 3 | 15.0 |
| | Pyrophyllite (20/40) | 70.0 |
| | | 100.0 |

V. Microcapsules

| A. | DPX-M6316 | 35.0 |
|---|---|---|
| | Acetochlor encapsulated in polyurea shell wall | 15.0 |
| | Antidote No. 1 | |
| | Sodium lignosulfonate (e.g., Reax 88 ® B) | 0.9 |
| | Water | 14.1 |
| | | 100.0 |
| B. | Chlorsulfuron | 25.0 |
| | Alachlor encapsulated in polyurea shell wall | 15.0 |
| | Antidote No. 2 | 30.0 |
| | Potassium lignosulfonate (e.g., Reax ® C-21) | 0.5 |
| | Water | 29.5 |
| | | 100.0 |
| C. | Chlorimuron ethyl | 20.0 |
| | Metolachlor encapsulated in polyurea shell wall | 15.0 |
| | Antidote No. 2 | 40.0 |
| | Magnesium salt of lignosulfate (Treax, LTM ®) | 2.0 |
| | Water | 23.0 |
| | | 100.0 |
| D. | Triasulfuron | 15.0 |
| | Alachlor ⎫ encapsulated in | 15.0 |
| | Antidote No. 1 ⎬ a polyurea shell wall | 35.0 |
| | Potassium lignosulfinate (Reax ®-C-21) | 0.8 |
| | Water | 34.2 |
| | | 100.0 |
| E. | Sulfometuron | 20.0 |
| | Alachlor ⎫ encapsulated in | 20.0 |
| | Antidote No. 1 ⎬ a polyurea shell wall | 25.0 |
| | Sodium lignosulfonate (e.g., Reax 88 ® B) | 0.5 |
| | Water | 34.5 |
| | | 100.0 |
| F. | DPX-M6316 | 5.0 |
| | Acetochlor encapsulated in a polyurea shell wall | 16.0 |
| | Antidote No. 2 | 20.0 |
| | Reax ® C-21 | 5.0 |
| | Water | 54.0 |
| | | 100.0 |
| G. | Chlorsulfuron | 4.5 |
| | Alachlor encapsulated in a polyurea shell wall | 15.0 |
| | Antidote No. 2 | 15.0 |
| | Treax, LTM ® | 3.0 |
| | Water | 63.0 |
| | | 100.0 |
| H. | Chlorimuron | 10.0 |
| | Metolachlor encapsulated in a polyurea shell wall | 12.0 |
| | Antidote No. 1 | 25.0 |
| | Reax C-21 | 1.0 |
| | Water | 52.0 |
| | | 100.0 |

-continued

|  |  | Weight Percent |
|---|---|---|
| I. | Sulfometuron | 8.0 |
|  | Acetochlor encapsulated in a polyurea shell wall | 16.0 |
|  | Antidote No. 1 | 10.0 |
|  | Reax 88 ® B | 1.0 |
|  | Water | 55.0 |
|  |  | 100.0 |

It will be understood by those skilled in the art that certain combinations of a sulfonylurea with a particular acetanilide or other co-herbicide and/or antidote may be incompatible with each other in one or another liquid media, hence rendering some formulations unfeasible. For example, sulfometuron (active ingredient in OUST ® herbicide) should not be mixed with high pH herbicides. Some of these co-herbicide combinations may be found to be incompatible, or have a short shelf-life and this is readily determined without undue experimentation by those skilled in the art.

Suitable carriers for many of the herbicides and antidotes disclosed herein include common ketone, alcohol, hydrocarbon-based solvents, e.g., acetone, dimethyl sulfoxide, n-heptane, methanol, methylene chloride, cyclohexane, toluene, etc.

The above specifically mentioned sulfonylurea and α-haloacetanilide herbicidal compounds used as co-herbicides herein are intended merely as exemplary of the classes of herbicides which they represent. However, it is expressly contemplated that many other herbicidal compounds analogous to those represented herein having a variety of equivalent radicals substituted on the central nucleus may similarly be safened to various crop plants to a greater or lesser extent with the antidotal compounds of this invention. For example, other α-haloacetanilide compounds useful as herbicides are described in U.S. Pat. Nos. 3,442,945, 3,547,620, 3,830,841, 3,901,768, 4,517,011, 4,601,745, 4,319,918, 3,586,496, 3,574,746 and 4,249,935.

Other important herbicidal sulfonylureas specifically contemplated as useful as co-herbicides in compositions with the antidotal compounds of this invention include those disclosed in the following patents: U.S. Pat. Nos. 4,383,113, 4,127,405, 4,481,029, 4,514,212, 4,420,325, 4,638,004, 4,675,046, 4,681,620, 4,741,760, 4,723,123, 4,411,690, 4,718,937, 404,620,868, 4,668,277, 4,592,776, 4,666,508, 4,696,695, 4,731,446 and 4,668,279, 4,752,322, 4,875,923, 4,877,442, 4,878,937, 4,878,938 and 4,881,968; EP Numbers 084224, 173312, 190105, 256396, 264021, 264672, 142152, 244847, 176304, 177163, 187470, 187489, 184385, 232067, 234352, 189069, 224842, 249938, 246984 and 246984 and German Offen. DE 3,618,004.

Among the herbicidal sulfonylureas disclosed in one or more of the above patents which are of particular interest are mentioned the species N-[(4-methoxy-6-methylpyrimidin-2-yl)aminocarbonyl]-3-chloro-4-methoxycarbonyl-1-methylpyrazole-5-sulfonamide, N-[(4,6-dimethoxypyrimidin-2-yl)aminocarbonyl]-3-chloro-4-methoxycarbonyl-1-methylpyrazole-5-sulfonamide, N-[(4-methoxy-6-methylpyrimidin-2-yl)aminocarbonyl]-3-chloro-4-ethoxycarbonyl-1-methylpyrazole-5-sulfonamide, N-[(4,6-dimethoxypyrimidin-2-yl)aminocarbonyl]-3-chloro-4-ethoxycarbonyl-1-methylpyrazole-5-sulfonamide, N-[(4-methoxy-6-methylpyrimidin-2-yl)aminocarbonyl]-3-bromo-4-ethoxycarbonyl-1-methylpyrazole-5-sulfonamide, N-[(4,6-dimethoxypyrimidin-2-yl)aminocarbonyl]-3-bromo-4-ethoxycarbonyl-1-methylpyrazole-5-sulfonamide and N-(methoxycarbonyl-1-phenyl sulfonyl-N'-(bis-difluoromethoxy pyrimidin-2-yl)urea.

As will be appreciated by those skilled in the art, the practice of this invention contemplates the use of the antidotal compounds according to Formula III above with any herbicidally-active combination of sulfonylureas and α-haloacetanilides according to Formulae I and II, respectively as co-herbicides. Obviously, the above listings of exemplary compounds is not intended to be exhaustive, but representative. Again, as noted earlier herein, it is expected that not every combination of herbicide(s) and antidote(s) will result in safening of all crops, but is within the skill of the art to test any given herbicide combination with an antidote in accordance with Formula III in plant screens of any spectrum of plants and note the results.

The foregoing embodiments illustrate that the combinations of herbicide and antidote of this invention are useful in controlling weeds while reducing herbicidal injury to crop plants under greenhouse test conditions.

In field applications, the herbicide, antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide(s) and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of emulsifiable concentrates, microencapsulates, particulate solids, granules of varying particle size, e.g., water-dispersible or water-soluble granules or larger dry granules, pellets, wettable powders, dusts, solutions, aqueous dispersions, or emulsions.

Examples of suitable adjuvants are finely-divided solid carriers and extenders including talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powders usually contain as a conditioning agent one or more surface-active agents in amounts sufficient to make a composition readily dispersible in water or in oil. The term "surface-active agent" includes wetting agents, dispersing agents, suspending agents, and emulsifying agents. Typical surface-active agents are mentioned in U.S. Pat. No. 2,547,724.

Compositions of this invention generally contain from about 5 to 95 parts herbicide-and-antidote, about 1 to 50 parts surface-active agent, and about 4 to 94 parts solvent, all parts being by weight based on the total weight of the composition.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10 0 parts of antidote per 1000 parts of seed. Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seed-coating or for antidotes applied to soil in granular or liquid formulations, suitable carriers may be either solids, such as talc, sand, clay, diatomaceous earth, sawdust, calcium carbonate, and the like, or liquids, such as water, kerosene, acetone, benzene, toluene, xylene, and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher-alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8–18 carbon atoms, long-chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, long-chain alcohols usually containing 10–18 carbon atoms, and condensation products of ethylene oxide with fatty acids, alkylphenols, and mercaptans.

Although this invention has been described with respect to specific embodiments, the details of these embodiments are not to be construed as limitations. Various equivalents, changes, and modifications may be made without departing from the spirit and scope of this invention, and it is understood that such equivalent embodiments are part of this invention.

I claim:

1. Herbicidal composition comprising
   (a) a herbicidally-effective amount of a sulfonylurea of the formula

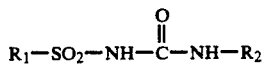

wherein $R_1$ and $R_2$ are independently phenyl, a heterocyclic radical containing up to 10 ring members of which 4 may be O, S or N atoms or said phenyl and heterocyclic radical optionally substituted with halogen, $C_{1-4}$ alkyl, haloalkyl, alkoxy, carboxyl or carboalkoxy radicals;

(b) a herbicidally-effective amount of an acetanilide of the formula

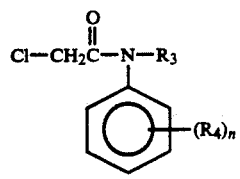

$R_3$ is hydrogen, $C_{1-8}$ alkyl, haloalkyl, alkoxy or alkoxyalkyl, alkenyl, haloalkenyl, alkynyl or haloalkynyl or acylamidoalkyl, having up to 6 carbon atoms, $C_{5-10}$ heterocyclyl or heterocyclylmethyl having O, S and/or N atoms and which may be substituted with halogen, $C_{1-4}$ alkyl, carbonylalkyl or carbonylalkoxyalkyl, nitro, amino or cyano groups;

$R_4$ is hydrogen, halogen, nitro, amino, $C_{1-6}$ alkyl, haloalkyl, alkoxy or alkoxyalkyl; and n is 0–5 and (c) an antidotally-effective amount of a compound of the formula

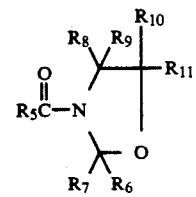

and agriculturally-acceptable salts thereof
wherein $R_5$ is halomethyl;

$R_6$ and $R_7$ are H, $C_{1-4}$ alkyl, haloalkyl, alkoxy or phenyl;

$R_{8-10}$ are H or $C_{1-4}$ alkyl;

$R_{11}$ is a saturated or unsaturated heterocyclic radical containing up to 10 ring atoms of which 3 may be O, S or N atoms, optionally substituted with halogen, $C_{1-4}$ alkyl, haloalkyl, alkoxy or alkoxyalkyl or with oxygen on a ring N atom or $R_{11}$ may be a bicyclic hydrocarbon radical containing up to 10 carbon atoms; and $R_{10}$ and $R_{11}$ may be combined to form a spiroheterocyclic ring as defined for $R_{11}$.

2. Composition according to claim 1 wherein said sulfonylurea is selected from the group consisting of:

Benzenesulfonamide, 2-chloro-N-[[(4-methoxy-6-methyl-1,3,5-triazin-2-yl)amino]carbonyl];

Benzoic acid, 2-[[[[(4-chloro-6-methoxy-2-pyrimidinyl)amino]carbonyl]amino]sulfonyl]ethyl ester;

2-Thiophenecarboxylic acid, 3-[[[[(4,6-dimethoxy-1,3,5-triazin-2-yl)amino]carbonyl]amino]sulfonyl]-, methyl ester;

Benzoic acid, 2-[[[[(4,6-dimethyl-2-pyrimidinyl)amino]carbonyl]amino]sulfonyl]methyl ester;

Benzenesulfonamide, 2-(2-chloroethoxy)-N-[[(4-methoxy-6-methyl-1,3,5-triazin-2-yl) amino]carbonyl]; and Benzoic acid, 2-[[[[(4-methoxy-6-methyl-1,3,5-triazin-2-yl)amino]carbonyl]amino]sulfonyl]methyl ester;

3. Composition according to claim 2 wherein in said compound of Formula II, $R_3$ is a $C_{1-8}$ alkoxyalkyl or N-containing heterocyclylmethyl radical and $R_4$ is a $C_{1-4}$ alkyl radical.

4. Composition according to claim 3 wherein in said compound of Formula III, $R_5$ is chloromethyl and $R_6$ and $R_7$ are $C_{1-4}$ alkyl or haloalkyl.

5. Composition according to claim 4 wherein said acetanilide is selected from the group consisting of
acetochlor,
alachlor,
butachlor,
metazachlor,
metolachlor and
pretilachlor.

6. Composition according to claim 5 wherein said antidotal compound is selected from the group consisting of Oxazolidine, 3-(dichloroacetyl)-2,2-dimethyl-5-(2-furanyl)-,
Oxazolidine, 3-(dichloroacetyl)-2,2-dimethyl-5-(2-thienyl)-,
Pyridine, 3-[3-(dichloroacetyl)-2,2-dimethyl-5-oxazolidinyl]-.

7. Composition according to any one of claims 2–5 or 6 wherein said sulfonylurea is DPX-M6316 or chlorimuron ethyl, said acetanilide is acetochlor or alachlor and said antidotal compound is oxazolidine, 3-(dichloroacetyl)-2,2-dimethyl-5-(2-furanyl)-.

8. Composition according to claim 7 comprising DPX-M6316, acetochlor and oxazolidine, 3-(dichloroacetyl)-2,2-dimethyl-5-(2-furanyl).

9. Composition according to claim 7 comprising chlorimuron ethyl, acetochlor and oxazolidine, 3-(dichloroacetyl)-2,2-dimethyl-5-(2-furanyl).

10. Method for reducing phytotoxicity to crop plants due to mixtures of sulfonylurea herbicides having the formula

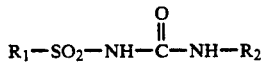

I wherein $R_1$ and $R_2$ are independently phenyl, a heterocyclic radical containing up to 10 ring members of which 4 may be O, S or N atoms or said phenyl and heterocyclic radical optionally substituted with halogen, $C_{1-4}$ alkyl, haloalkyl, alkoxy, carboxyl or carboalkoxy radicals;
and acetanilide herbicides having the formula

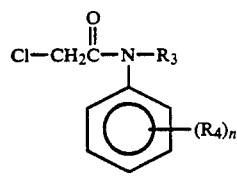

II wherein
$R_3$ is hydrogen, $C_{1-8}$ alkyl, haloalkyl, alkoxy or alkoxyalkyl, alkenyl, haloalkenyl, alkynyl or haloalkynyl or acylamidoalkyl, having up to 6 carbon atoms, $C_{5-10}$ heterocyclyl or heterocyclylmethyl having O, S and/or N atoms and which may be substituted with halogen, $C_{1-4}$ alkyl, carbonylalkyl or carbonylalkoxyalkyl, nitro, amino or cyano groups;
$R_4$ is hydrogen, halogen, nitro, amino, $C_{1-6}$ alkyl, haloalkyl, alkoxy or alkoxyalkyl; and
n is 0–5
which comprises applying to the locus of the crop plant an antidotally-effective amount of a compound of the formula

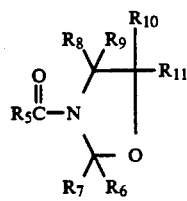

III and agriculturally-acceptable salts thereof
wherein $R_5$ is halomethyl;
$R_6$ and $R_7$ are H, $C_{1-4}$ alkyl, haloalkyl, alkoxy or phenyl;
$R_{8-10}$ are H or $C_{1-4}$ alkyl;
$R_{11}$ is a saturated or unsaturated heterocyclic radical containing up to 10 ring atoms of which 3 may be O, S or N atoms, optionally substituted with halogen, $C_{1-4}$ alkyl, haloalkyl, alkoxy or alkoxyalkyl or with oxygen on a ring N atom or $R_{11}$ may be a bicyclic hydrocarbon radical containing up to 10 carbon atoms; and
$R_{10}$ and $R_{11}$ may be combined to form a spiroheterocyclic ring as defined for $R_{11}$.

11. Method according to claim 10 wherein said sulfonylurea is selected from the group consisting of
Benzenesulfonamide, 2-chloro-N-[[(4-methoxy-6-methyl-1,3,5-triazin-2-yl)amino]carbonyl];
Benzoic acid, 2-[[[[(4-chloro-6-methoxy-2-pyrimidinyl)amino]carbonyl]amino]sulfonyl]ethyl ester;
2-Thiophenecarboxylic acid, 3-[[[[(4,6-dimethoxy-1,3,5-triazin-2-yl)amino]carbonyl]amino]sulfonyl]-, methyl ester;
Benzoic acid, 2-[[[[(4,6-dimethyl-2-pyrimidinyl)amino]carbonyl]amino]sulfonyl]methyl ester;
Benzenesulfonamide, 2-(2-chloroethoxy)-N-[[(4-methoxy-6-methyl-1,3,5-triazin-2-yl) amino]carbonyl]; and
Benzoic acid, 2-[[[[(4-methoxy-6-methyl-1,3,5-triazin-2-yl)amino]carbonyl]amino]sulfonyl]methyl ester;

12. Method according to claim 11 wherein in said acetanilide of Formula II, $R_3$ is a $C_{1-8}$ s alkoxyalkyl or N-containing heterocyclylmethyl radical and $R_4$ is a $C_{1-4}$ alkyl radical.

13. Method according to claim 12 wherein in said compound of Formula III, $R_5$ is chloromethyl and $R_6$ and $R_7$ are $C_{1-4}$ alkyl or haloalkyl.

14. Method according to claim 13 wherein said acetanilide is selected from the group consisting of
acetochlor,
alachlor,
butachlor,
metazachlor,
metolachlor and
pretilachlor.

15. Method according to claim 14 wherein said antidotal compound is selected from the group consisting of
Oxazolidine, 3-(dichloroacetyl)-2,2-dimethyl-5-(2-furanyl)-, Oxazolidine, 3-(dichloroacetyl)-2,2-dimethyl-5-(2-thienyl)-, Pyridine, 3-[3-(dichloroacetyl)-2,2-dimethyl-5-oxazolidinyl]-.

16. Method according to any one of claims 11–14 or 15 wherein said sulfonylurea is DPX-M6316 or chlorimuron ethyl, said acetanilide is acetochlor or alachlor and said antidotal compound is oxazolidine, 3-(dichloroacetyl)-2,2-dimethyl-5-(2-furanyl)-.

17. Method according to claim 16 wherein said mixture comprises DPX-M6316 and acetochlor and oxazolidine, 3-(dichloroacetyl)-2,2-dimethyl-5-(2-furanyl)-.

18. Method according to claim 16 wherein said mixture comprises chlorimuron and acetochlor and said antidotal compound is oxazolidine, 3-(dichloroacetyl)-2,2-dimethyl-5-(2-furanyl)-.

19. Method according to any one of claims 11–17 or 18 wherein said crop plant is corn.

* * * * *